(12) United States Patent
Taekema et al.

(10) Patent No.: US 7,568,668 B2
(45) Date of Patent: Aug. 4, 2009

(54) FOLDABLE STAND

(75) Inventors: Harko Jan Taekema, Eindhoven (NL); Rogier Hille, Groningen (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 351 days.

(21) Appl. No.: 10/561,455

(22) PCT Filed: Jun. 22, 2004

(86) PCT No.: PCT/IB2004/050963

§ 371 (c)(1),
(2), (4) Date: Dec. 20, 2005

(87) PCT Pub. No.: WO2004/113783

PCT Pub. Date: Dec. 29, 2004

(65) Prior Publication Data

US 2007/0145206 A1    Jun. 28, 2007

(30) Foreign Application Priority Data

Jun. 25, 2003    (EP) .................................. 03101887

(51) Int. Cl.
    *F16M 11/38*    (2006.01)
(52) U.S. Cl. ..................................... 248/166
(58) Field of Classification Search ................. 248/150, 248/151, 137, 166, 127; 16/37
    See application file for complete search history.

(56) References Cited

U.S. PATENT DOCUMENTS

| 4,684,091 | A |   | 8/1987  | Moreschi |
| 4,866,284 | A |   | 9/1989  | Frankena et al. |
| 5,197,701 | A |   | 3/1993  | Olsen |
| 5,320,227 | A | * | 6/1994  | Minoura ....................... 211/22 |
| 5,996,814 | A |   | 12/1999 | Workman |
| 6,254,044 | B1 | * | 7/2001 | Lee ........................... 248/177.1 |
| 6,789,772 | B2 | * | 9/2004 | Eason .......................... 248/166 |
| 2005/0051682 | A1 | * | 3/2005 | Tuohy et al. .............. 248/176.1 |

\* cited by examiner

*Primary Examiner*—Ramon O Ramirez

(57) ABSTRACT

The invention relates to a foldable stand (1) comprising a longitudinally extending support (2) which is carried by two legs (3), each leg (3) being connected to the support (2) via a journal (4) having a central axis (5), said stand (1) being foldable between an operational position, in which the legs (3) extend in one plane and the support (2) extends away from said plane and a rest position in which the legs (3) extend in said plane and the support (2) also extends in said plane substantially parallel to the legs (3), wherein a housing (6) is provided to which the support (2) is fixedly mounted, and a coupling element (7) is provided in said housing (6) for rotationally coupling the central axes (5) of the journals (4) of the legs (3) at an angle relative to each other. Folding of the stand between the operational position and the rest position requires only one operation from a user. By moving the support from its operational position the legs are automatically taken along from said operational position into said rest position.

13 Claims, 5 Drawing Sheets

FOLDABLE STAND

Figure 1A:
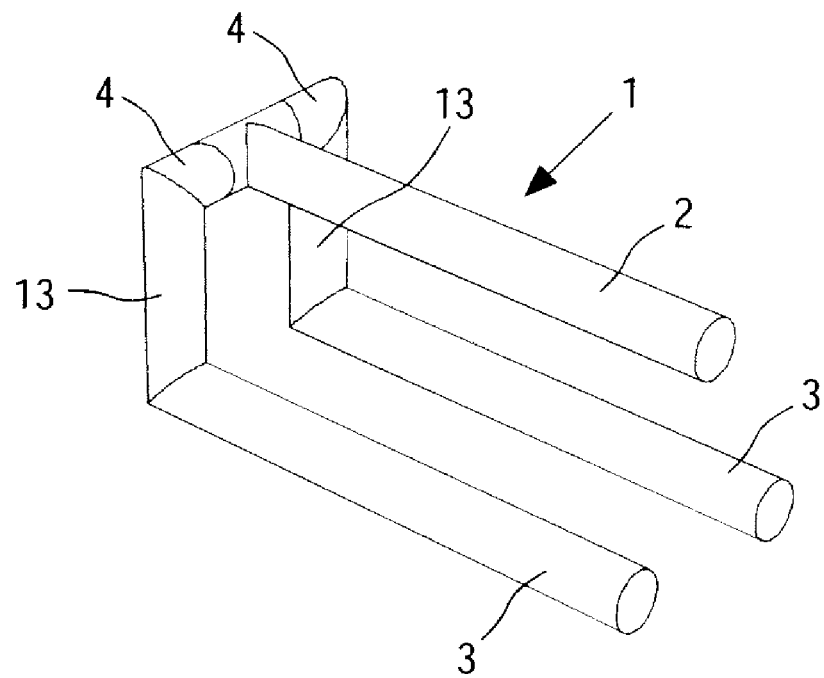

The invention relates to a foldable stand comprising a longitudinally extending support which is carried by two legs, each leg being connected to the support via a journal having a central axis, said stand being foldable between an operational position in which the legs extend in one plane and the support extends away from said plane and a rest position in which the legs extend in said plane and the support also extends in said plane substantially parallel to the legs.

The invention further relates to an irradiation device for the human body comprising such a foldable stand.

A foldable stand of the type described in the opening paragraph is known from U.S. Pat. No. 4,866,284. This known foldable stand is comprised in an irradiation device for irradiating the human body with ultraviolet radiation. The support is pivotally connected to a wide base for stable positioning of the device on a surface. Said base comprises a recess for receiving the support in the rest position, thus forming two legs. The support further carries a housing provided with an irradiation unit which is pivotally connected to the support. During operation, the legs support the device on the surface in a stable position by extending in one plane along the surface, and the support extends away from the surface. Ultraviolet radiation leaves the housing through a radiation emission window which extends in a horizontal plane. After use, the housing and the support are rotated into a rest position extending substantially parallel to the legs along the surface, the support being received in the recess between the legs. Although this known stand is relatively compact in the folded position, the stand is relatively complex to fold. This is cumbersome for the user.

It is an object of the invention to provide a foldable stand which is easily foldable. To achieve this object, a foldable stand according to the invention is characterized in that a housing is provided to which the support is fixedly mounted, and a coupling element is provided in said housing for rotationally coupling the central axes of the journals of the legs at an angle relative to each other. In this manner, folding of the stand between the operational position and the rest position requires only one operation from a user. By moving the support from its operational position extending away from the plane into its rest position lying in the plane, the legs are automatically taken along from an operational position in the plane and enclosing an angle between them into a rest position in the plane and substantially parallel to each other. When the support is moved back again from the rest position into the operational position, the legs are automatically taken along from their position in the plane and substantially parallel to each other into their position in the plane and enclosing an angle between them. The foldable stand is thus easily foldable and user-friendly. Furthermore, the fact that the legs enclose an angle between them in the operational position ensures a stable position of the stand on the surface without the need for a heavy construction of the legs.

An embodiment of a foldable stand according to the invention is characterized in that each journal has a semi-cylindrical recess for cooperation with a semi-cylindrical protrusion provided on the coupling element by means of sliding and rotating surfaces. This offers a simple construction of the journals and the coupling element, because sliding and rotation is combined in one action so as to secure that the legs are moving simultaneously.

A further embodiment of a foldable stand according to the invention is characterized in that the coupling element has a central axis and comprises two cylindrical parts arranged in parallel and extending transversally to said central axis, the central axis of the coupling element intersecting a central axis of at least one journal at the center of at least one cylindrical part. In this manner the housing is less heavily loaded and the coupling element does not need a special bearing in the housing.

It is advantageous when the stand has elements for supporting the stand in a storage position with the legs and the support extending parallel to each other. Thus the compact foldable stand can be stored upright without the need of a wall or the like to support it.

It is furthermore advantageous when the central axes of the legs enclose an angle of 30° in the operational position.

A further embodiment of a foldable stand according to the invention is characterized in that the coupling element comprises a central coupling shaft provided with longitudinally extending grooves along its outer surface, and the two journals are provided with bevelled teeth for cooperation with said grooves. In this manner a solid and cost-effective construction is achieved.

A further embodiment of a foldable stand according to the invention is characterized in that the central axis of the central coupling shaft, the longitudinal axis passing through both teeth, and the central axis of a bearing carrying the journals intersect in one point. In this manner the parts only move rotationally with respect to each other during operation, which renders the construction more robust.

The invention further relates to an irradiation device for the human body comprising a foldable stand, characterized in that said foldable stand is a stand according to the invention.

Figure 1B:
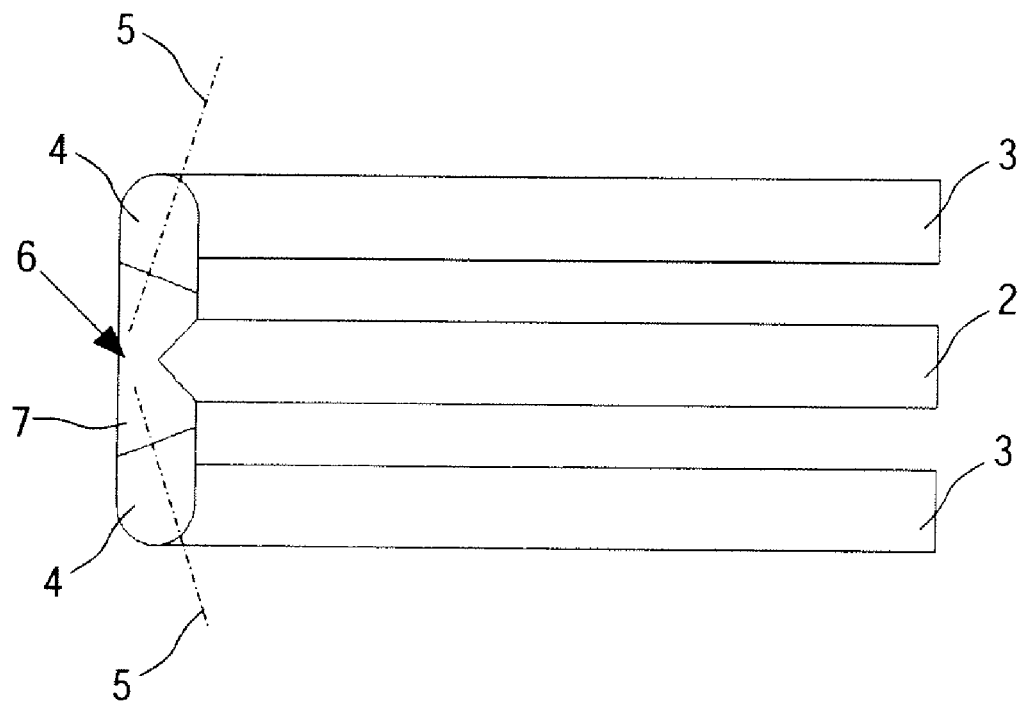
Figure 2A:
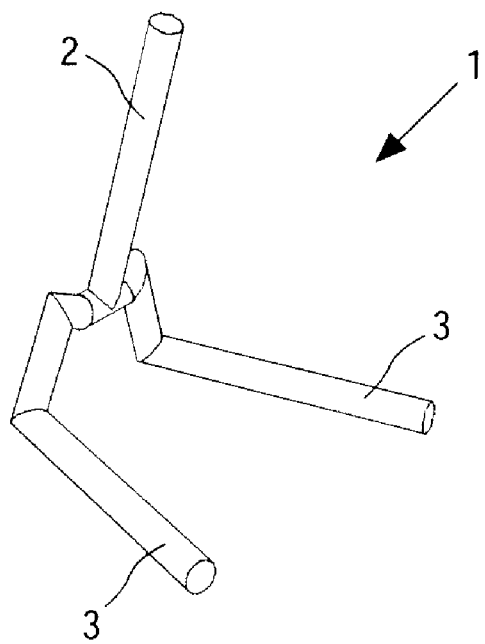
Figure 2B:
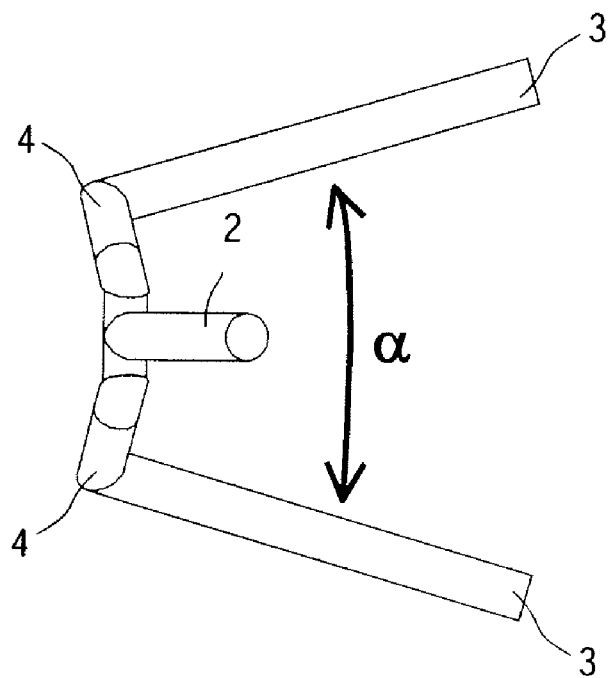
Figure 3A:
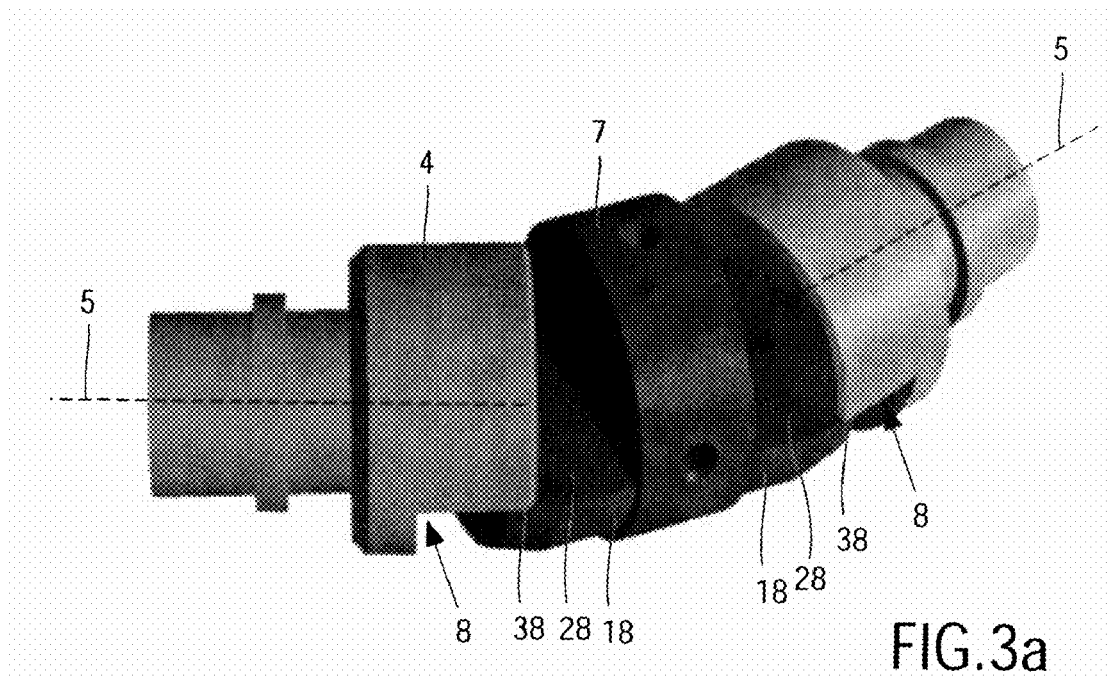
Figure 4:
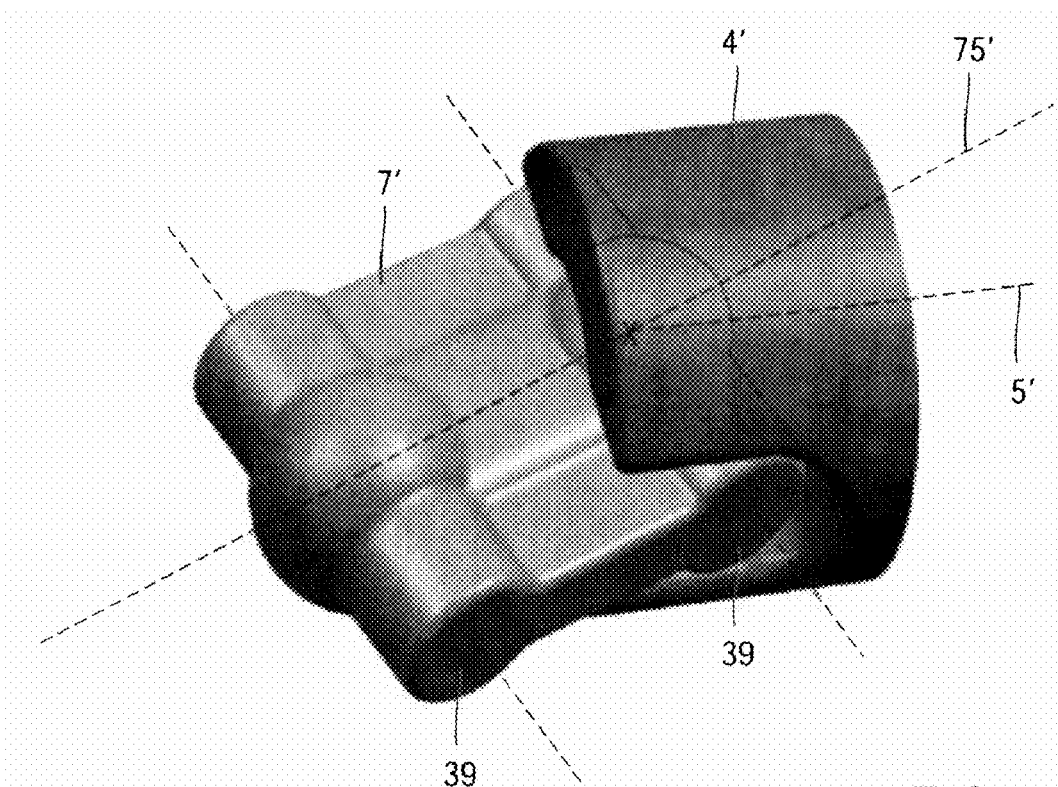

The invention will be described in more detail hereinafter with reference to the drawings, in which FIGS. 1a and 2a show a schematic perspective view of a foldable stand according to the invention in a rest position and in an operational position, respectively, and FIGS. 1b and 2b are plan views of said stand in a rest position and in an operational position, respectively, FIGS. 3a and b show a detail of a first embodiment of a foldable stand according to the invention, FIG. 4 shows a detail of a second embodiment of a foldable stand according to the invention, and FIGS. 5a, b and c show details of a third embodiment of a foldable stand according to the invention.

FIG. 1 shows different schematic views of a foldable stand 1 according to the invention, in a rest position (FIGS. 1a, b) and an operational position (FIGS. 2a, b). The foldable stand 1 comprises a longitudinally extending support 2 which is carried by two legs 3, each leg 3 being connected to the support 2 via a journal 4 having a central axis 5. A housing 6 is provided to which the support 2 is fixedly mounted, and a coupling element 7 is provided in said housing 6 for rotationally coupling the central axes 5 of the journals 4 of the legs 3 at an angle relative to each other. In this manner, the stand 1 can be folded by a user in only one operation between the operational position, in which the legs 3 extend in one plane and enclose an angle between them and the support 2 extends away from said plane and the rest position, in which the legs extend in said plane substantially parallel to each other and the support also extends in said plane substantially parallel to the legs. The foldable stand can thus be folded in an easy and user-friendly manner.

Furthermore, the legs enclose an angle α between them in the operational position, while extending in said plane along a surface. Thus a stable position of the stand on a support surface is ensured while the legs have a relatively light construction. As can be seen in FIG. 1a, this results in a compact foldable stand in its rest position which is easy to store. It is advantageous when the legs enclose an angle of 30° between them in the operational position.

In this embodiment, the stand has elements 13 for supporting the stand in a storage position with the legs and the support extending parallel to each other. This storage position may be, for example, the position of the stand in FIG. 1a, rotated through 90° resting on elements 13 which then extend along the support surface. In this manner the folded stand can be easily stored away, for example in a closet or the like. These elements, but also the legs themselves, may be provided with wheels in order to make the folded stand easily movable in its rest position.

FIGS 3a and b show a detail of a first embodiment of a foldable stand according to the invention. In this embodiment, each journal 4 has a semi-cylindrical recess 8 for cooperation with a semi-cylindrical protrusion 18 provided on the coupling element 7 by means of sliding surfaces 28 and rotating surfaces 38. In this embodiment, the rotating surfaces are provided as rounded edges 38 on the semi-cylindrical recesses 8 of the journals 4 which cooperate with the sliding surfaces 28, but these rounded surfaces may alternatively be provided as rounded edges on the semi-cylindrical protrusions 18 provided on the coupling element 7.

Figure 3B:
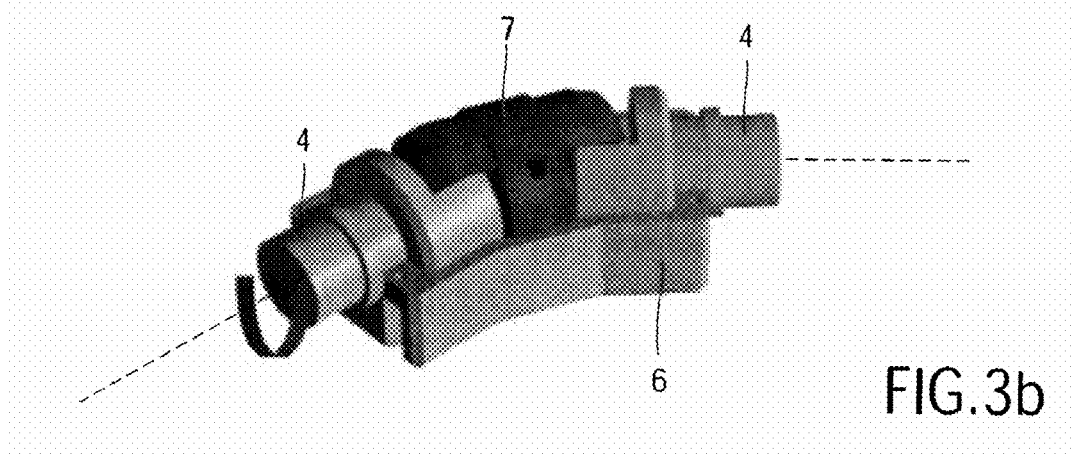

FIG. 3b shows a position occurring during movement of the legs 3 in which the journals 4 slide over the cooperating sliding surfaces 28 and simultaneously rotate via the rotating surfaces 38. In this embodiment sliding and rotation is combined in one action, to ensure that the legs are moving simultaneously. This offers a simple construction of the journals and the coupling element.

FIG. 4 shows a detail of a second embodiment of a foldable stand 1' according to the invention, in which the coupling element 7' has a central axis 75' and comprises two cylindrical parts 39 arranged in parallel and extending transversally to said central axis 75', the central axis 75' of the coupling element 7' intersecting a central axis 5' of at least one journal 4' at the center of at least one cylindrical part. For reasons of clarity, only one of the journals 4' is shown in the Figure. This construction is advantageous because it is relatively simple, the housing is less heavily loaded, and the coupling element needs no bearings in the housing.

Figure 5A:
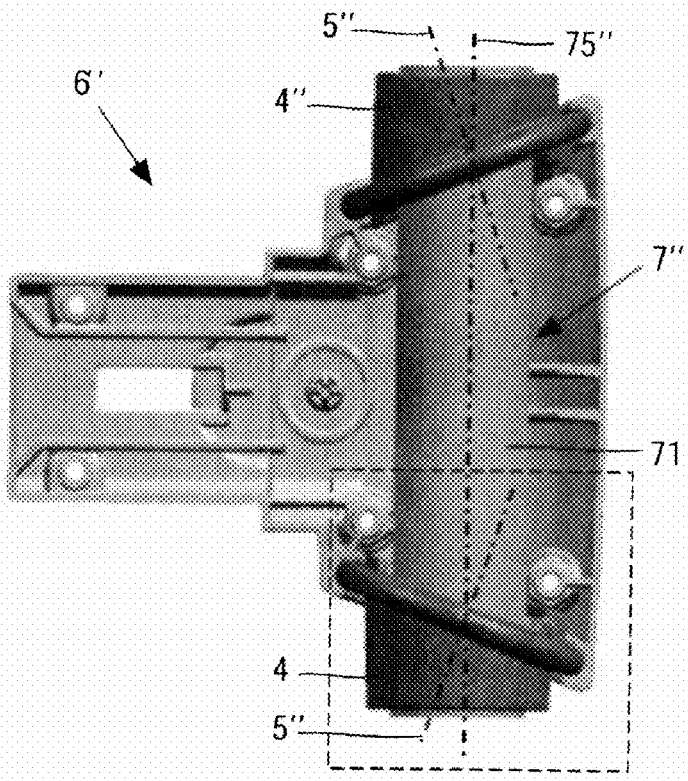
Figure 5B:
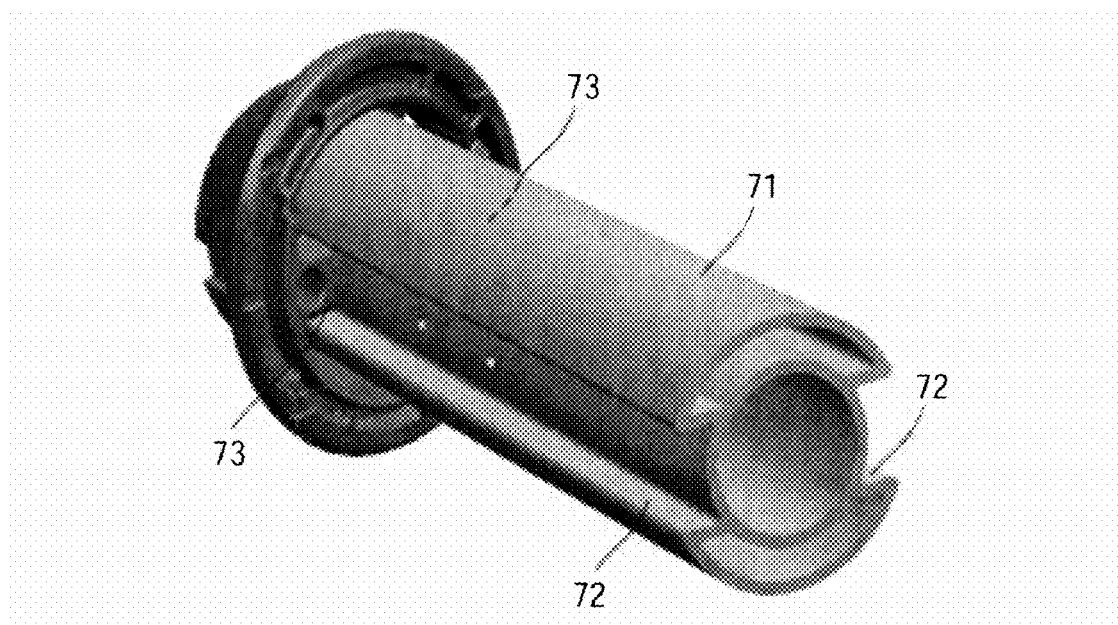

FIGS. 5a, b and c show details of a third embodiment of a foldable stand 1" according to the invention. FIG. 5a is a top view of the housing 6" in which the coupling element 7" is provided for rotationally coupling the central axes 5" of the journals 4" of the legs 13" at an angle relative to each other. As can be seen in more detail in FIG. 5b, the coupling element 7" comprises a central coupling shaft 71 provided with longitudinally extending grooves 72 along its outer surface, and the two journals 4" are provided with bevelled teeth 73 for cooperation with said grooves 72. For reasons of clarity, only one of the journals 4" is shown in the Figure. This construction is advantageous because it is solid and cost-effective.

Figure 5C:
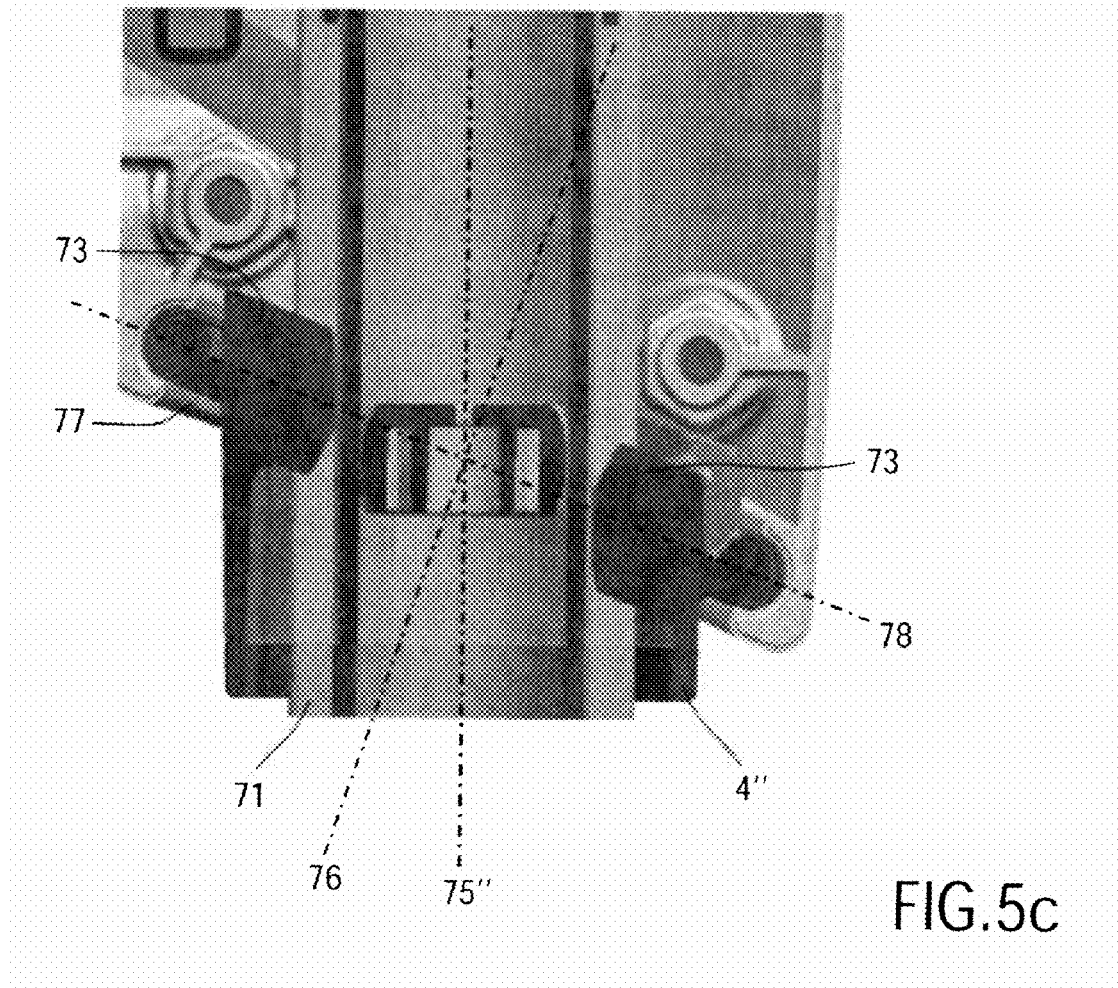

FIG. 5c shows a further detail of the third embodiment of a foldable stand 1" according to the invention, as enclosed by a broken-line square in FIG. 5a. The central axis 75" of the central coupling shaft 71, the longitudinal axis 78 passing through both teeth 73, and the central axis 76 of a bearing 77 carrying the journal 4" intersect in one point. In this manner the parts only move rotationally with respect to each other during operation, which renders the construction more robust.

It is observed that the foldable stand according to the invention is especially suitable for use in an irradiation device for the human body. However, the foldable stand according to the invention is also suitable for use with other types of irradiation devices, or for supporting other elements such as, for example, a screen.

When the foldable stand according to the invention carries an element, it is noted that it is advantageous when the element carried by the stand is provided in a plane above the location of the legs in the operational position. Especially when the foldable stand according to the invention is used with an irradiation device for the human body, it is noted that it is advantageous when the housing with the irradiation unit is provided in a plane above the location of the legs in the operational position. When the user is lying on a bed during use of the irradiation device, the legs can thus be positioned under the bed during operation. In this manner the legs are not in the way and the space around the bed is left clear.

The invention claimed is:

1. A foldable stand, comprising:
   a longitudinally extending support which is carried by two legs, each leg being connected to the support by a rotatable connection,
   the stand being foldable between an operational position, in which the legs extend in a plane and the support extends away from the plane, and
   a rest position in which the legs extend in the plane and the support extends substantially parallel to the plane and the legs, wherein the rotatable connection is configured to maintain the two legs in the plane while the foldable stand is transitioned between the operational position and the rest position.

2. The foldable stand as claimed in claim 1, comprising:
   a housing fixedly mounted to the support; and
   two journals, wherein each journal is connected to a corresponding one of the two legs, wherein each journal has a semi-cylindrical recess for cooperation with a corresponding semi-cylindrical protrusion provided on the housing by means of sliding and rotating surfaces.

3. The foldable stand as claimed in claim 1, wherein the stand has elements for supporting the stand in a storage position with the legs and the support extending parallel to each other.

4. The foldable stand as claimed in claim 1, wherein the legs enclose an angle of 30° in the operational position.

5. The foldable stand as claimed in claim 1, comprising an irradiation device for the human body coupled to the support.

6. A foldable stand, comprising
   a longitudinally extending support which is carried by two legs, each leg being connected to the support via a journal having a central axis,
   said stand being foldable between an operational position, in which the legs extend in one plane the support extends away from said plane, and
   a rest position in which the legs extend in said plane and the support also extends in said plane substantially parallel to the legs,
   wherein a housing is provided to which the support is fixedly mounted, and a coupling element is provided in said housing for rotationally coupling the central axes of the journals of the legs at an angle relative to each other, wherein the coupling element and the journals together are configured to maintain the legs in said one plane while the stand is adjusted between the rest and operational positions, wherein the coupling element comprises a central coupling shaft provided with longitudinally extending grooves along its outer surface, and the two journals are provided with bevelled teeth for cooperation with said grooves.

7. The foldable stand as claimed in claim 6, wherein the central axis of the central coupling shaft, the longitudinal axis passing through both teeth, and the central axis of a bearing carrying the journal intersect in one point.

8. A foldable stand, comprising
a longitudinally extending support which is carried by two legs, each leg being connected to the support via a journal having a central axis,
said stand being foldable between an operational position, in which the legs extend in one plane the support extends away from said plane, and
a rest position in which the legs extend in said plane and the support also extends in said plane substantially parallel to the legs,
wherein a housing is provided to which the support is fixedly mounted, and a coupling element is provided in said housing for rotationally coupling the central axes of the journals of the legs at an angle relative to each other, wherein the coupling element and the journals together are configured to maintain the legs in said one plane while the stand is adjusted between the rest and operational positions, wherein the coupling element has a central axis and comprises two cylindrical parts arranged in parallel and extending transversally to said central axis, the central axis of the coupling element intersecting a central axis of at least one journal at the center of at least one cylindrical part.

9. A foldable stand, comprising
a longitudinally extending support which is carried by two legs, each leg being connected to the support via a journal having a central axis,
said stand being foldable between an operational position, in which the legs extend in one plane the support extends away from said plane, and
a rest position in which the legs extend in said plane and the support also extends in said plane substantially parallel to the legs, wherein a housing is provided to which the support is fixedly mounted, and a coupling element is provided in said housing for rotationally coupling the central axes of the journals of the legs at an angle relative to each other, and wherein the coupling element has a central axis and comprises two cylindrical parts arranged in parallel and extending transversally to said central axis, the central axis of the coupling element intersecting a central axis of at least one journal at the center of at least one cylindrical part.

10. A foldable stand, comprising
a longitudinally extending support which is carried by two legs, each leg being connected to the support via a journal having a central axis,
said stand being foldable between an operational position, in which the legs extend in one plane the support extends away from said plane, and
a rest position in which the legs extend in said plane and the support also extends in said plane substantially parallel to the legs, wherein a housing is provided to which the support is fixedly mounted, and a coupling element is provided in said housing for rotationally coupling the central axes of the journals of the legs at an angle relative to each other, and wherein the coupling element comprises a central coupling shaft provided with longitudinally extending grooves along its outer surface, and the two journals are provided with beveled teeth for cooperation with said grooves.

11. The foldable stand as claimed in claim 10, wherein the central axis of the central coupling shaft, the longitudinal axis passing through both teeth, and the central axis of a bearing carrying the journal intersect in one point.

12. A foldable stand, comprising:
a longitudinal extending support which is carried by two legs, each leg being connected to the support by a rotatable connection,
a housing fixedly mounted to the support, and
two journals, wherein each journal is connected to a corresponding one of the two legs, wherein each journal has a semi-cylindrical recess for cooperation with a corresponding semi-cylindrical protrusion provided on the housing by means of sliding and rotating surfaces,
the stand being foldable between an operational position, in which the legs extend in a plane and the support extend away from the plane, and
a rest position in which the legs extend in the plane and the support extends substantially parallel to the plane and the legs, wherein the rotatable connection is configured to maintain the two legs in the plane while the foldable stand is transitioned between the operational positioning and the rest position.

13. A foldable stand, comprising:
a longitudinal extending support which is carried by two legs, each leg being connected to the support by a rotatable connection, and two journals, wherein each journal is connected to a corresponding one of the two legs, and wherein each journal is coupled to the support by a corresponding rotatable connection,
the stand being foldable between an operational position, in which the legs extend in a plane and the support extends away from the plane, and
a rest position in which the legs extend in the plane and the support extends substantially parallel to the plane and the legs, wherein the rotatable connection is configured to maintain the two legs in the plane while the foldable stand is transitioned between the operational position and the rest position.

* * * * *